United States Patent [19]

Van Den Oetelaar et al.

[11] Patent Number: 5,208,261
[45] Date of Patent: May 4, 1993

[54] STABILIZED SOLUTIONS OF PSYCHOTROPIC AGENTS

[75] Inventors: Petrus J. M. Van Den Oetelaar, Heesch; Maria M. F. Mentink, Oss, both of Netherlands

[73] Assignee: Akzo N.V., Arnhem, Netherlands

[21] Appl. No.: 769,312

[22] Filed: Oct. 1, 1991

Related U.S. Application Data

[62] Division of Ser. No. 621,480, Dec. 3, 1990, Pat. No. 5,082,864.

[30] Foreign Application Priority Data

Dec. 6, 1989 [EP] European Pat. Off. ........ 89203092.5

[51] Int. Cl.$^5$ ............................................ A61K 31/135
[52] U.S. Cl. .................................................... 514/646
[58] Field of Search ......................................... 514/646

Primary Examiner—S. J. Friedman
Attorney, Agent, or Firm—William M. Blackstone

[57] ABSTRACT

Disclosed are stabilized aqueous preparations containing an antidepressant in admixture with a stabilizing compound such as L-methionine, D-methionine, DL-methionine, or mixtures thereof. The stabilized preparations display better stability when exposed to light, relatively high temperatures, time, and peroxides resulting in longer shelf-lives. Antidepressants which are stabilized include mirtazapine, mianserin, septiline, and amitriptyline.

7 Claims, No Drawings

STABILIZED SOLUTIONS OF PSYCHOTROPIC AGENTS

This is a division of application Ser. No. 07/621,480 filed Dec. 3, 1990, now U.S. Pat. No. 5,082,864.

BACKGROUND OF THE INVENTION

1. Field

This invention relates to pharmaceutical compositions generally, and to stabilized aqueous solutions of certain antidepressant drugs specifically.

2. State of the Art

Solutions of certain antidepressants (e.g., amitriptyline) are not very stable. They discolor, form particles, and/or suffer a decrease in concentration under certain conditions. For example, they may discolor or show a decrease in concentration upon exposure to light; upon the formation of peroxides in, or addition of peroxides to, the solutions; or when such solutions are stored at elevated temperatures. Particles may also form in such solutions under these conditions. Discoloration, development of opalescence, a decrease in concentration, and particle formation are all tokens of instability. These tokens of instability may occur rather rapidly, sometimes within days, forcing the dispensing pharmacist to mix new solutions frequently.

An attempt to stabilize dry pharmaceutical preparations containing amitriptyline oxide dihydrate is described in German Patent Application DE 3247676 A1, published on Jun. 28, 1984 (corresponding to U.S. Pat. No. 4,567,202). That patent application describes a composition containing amitriptyline oxide dihydrate and an organic acid including certain listed amino acids. The organic acid, especially citric acid, is used to stabilize the amitriptyline.

GB 2,082,910A to Berk Pharmaceuticals Ltd. (published on Mar. 17, 1982) describes a pharmaceutical composition (e.g. a syrup) comprising amitriptyline and L-tryptophan in an inert carrier. The L-tryptophan reportedly acts to reduce side-effects associated with the amitriptyline.

EP 93,373A (corresponding to U.S. Pat. No. 4,603,131) to Abbott Laboratories describes a liquid pharmaceutical composition useful for preventing irritation of the nasal mucousal membrane. The composition contains a tri-cyclic antidepressant, certain buffers, and "preservatives". The preservatives listed include: benzalkonium chloride, edetate disodium, sodium bisulfate, phenylmercuric acetate, cetylpyridinium chloride, thimerosal, chlorobutamol, cetyltrimethyl ammonium bromide, methylparaben, propylparaben, and butylparaben.

SUMMARY OF THE INVENTION

Generally, the invention includes a stable aqueous preparation of a nitrogen containing heterocyclic compound in admixture with water and methionine (e.g. L-methionine ("L-MET")). The heterocyclic compound will generally be a tricyclic or tetracyclic antidepressant compound containing aromatic and non-aromatic rings. The particular heterocyclic compounds will be at least partially capable of stabilization by the particular stabilizer in aqueous systems. The preparation will contain a sufficient amount of stabilizer to stabilize the heterocyclic compound in aqueous solution for a desired time at a desired temperature.

DESCRIPTION OF THE PREFERRED EMBODIMENTS

Preferred heterocyclic compounds include mirtazapine (EXAMPLE I), mianserin (EXAMPLE II), amitriptyline HCl (EXAMPLE III), setipiline or "setiptilinum" (EXAMPLE IV), derivatives thereof, acid addition salts thereof, and mixtures thereof. These compounds are known antidepressant ("thymoleptic") compounds.

The heterocyclic compound ("heterocycle") used will be present in the aqueous preparations in sufficient concentrations to be therapeutically useful, either parenterally or orally, in the volume of aqueous preparation contemplated for use. As used herein, an aqueous preparation is a preparation containing water as a primary, but not necessarily the only, solvent. Useful doses for the heterocyclic compounds are well-known to medical practitioners. For example, 20 milliliters (ml) of an oral solution containing 5 milligrams/milliliter (mg/ml) of amitriptyline hydrochloride administered at bedtime may be sufficient to treat someone suffering from depression.

Especially preferred heterocyclic compounds for use with the stabilizer L-MET are mirtazapine and mianserin, due to these compounds' ability to be stabilized with that stabilizer.

Acid addition salts of the heterocycles are preferably used in the aqueous preparations mainly due to solubility considerations. Pharmacologically acceptable salts are preferably formed from a pharmacologically acceptable organic or inorganic acid such as hydrochloric, hydrobromic, fumaric ascorbic, tartaric, citric, lactic, maleic, palmitic, or other known acids. The hydrocloride salt is especially prefered.

As used herein, "stabilize" is a relative term. To stabilize with a stabilizing agent or compound means the ability to prevent or delay the onset of tokens of instability. For example, a solution would be deemed "stabilized" if, with the addition of a stabilizing compound ("stabilizer"), it took longer (e.g. 2 weeks instead of 1 week) to discolor in the presence of a destabilizing stimulus (e.g. storage of the solution at an elevated (40° C.) temperature).

Preferred stabilizers for use with the particular heterocylclic compounds are L-methionine, D-methionine, DL-methionine, and mixtures thereof. Primarily due to its relatively low toxicity in man, L-MET is especially preferred.

The concentration of stabilizer in solution will generally vary with the amount of time the solution is to be stabilized. For example, L-MET will generally be present in concentrations varying from about 0.05 mg/ml of solution to about 5 mg/ml. A concentration of 0.05 mg/ml is sufficient to an aqueous solution of mirtazapine at 60° C. in the dark for a few days, which may be sufficient for use in a hospital which compounds parenteral admixtures of the compound at or near the time of administration. A concentration of 0.1 mg/ml of L-MET is sufficient to stabilize a solution of mirtazapine at 60° C. in the dark for a little over one week. 0.25 mg/ ml of L-MET is sufficient to stabilize a solution of mirtazapine for 2 weeks at 60° C. in the dark. While, 0.5 mg/ml of L-MET is sufficient to stabilize a solution of mirtazapine for at least 4 weeks at 60° C., and for 6 months at 40° C. (106° F.) in the dark and for 12 months at 30° C. At the same time, 0.5 mg/ml of L-MET stabilizes an aqueous solution of amitriptyline HCl for only a little over one week in the presence of daylight. Furthermore, L-MET does not appear to stabilize the light induced degradation of another antidepressant compound, imipramine HCl, at least at the concentrations used.

Concentrations of D-methionine and DL-methionine will be similar to those of L-MET. The addition of a non-reducing sugar, such as sucrose, to the preparations may be useful in oral formulations to improve the flavor of the formulation. Sugars such as glucose or invert sugar should be avoided.

Methods for making aqueous formulations are well-known. Methods for making oral solutions, emulsions, and suspensions are described in Chase, et al, *Remington's Pharmaceutical Sciences*, pp. 1438–1462 (16th ed. 1980, Mack Publ. Co. of Easton, Pa., U.S.A.). Methods for making parenteral preparations and intravenous admixtures are disclosed in the same reference at pages 1463–1497. The aqueous pharmaceutical preparations are preferably buffered with citric acid.

Once the liquid pharmaceutical preparation is made, it is preferably packaged in light-resistant containers and kept in the dark.

The following examples further explain the invention:

EXAMPLE I

A. Stabilization of 1,2,3,4,10,14beta-hexahydro-2-methylpyrazino [2,1-a] pyrido [2,3-c][2] benzazepine with L-MET.

1,2,3,4,10,14beta-hexahydro-2-methylpyrazino [2,1-a] pyrido [2,3-c][2] ("mirtazapine") and similar compounds may be prepared as disclosed in U.S. Pat. No. 4,062,848 to van der Burg, the contents of which are incorporated by this reference. Aqueous solutions containing 3 mg/ml of the described anti-depressant compound (1.1 millimolar) were prepared. The solutions were buffered with citric acid to pH 4. The solutions further contained sufficient NaCl to make them iso-osmotic with blood.

1. Two weeks at 60° C. in the dark--Solutions of the described antidepressant compound also containing 0.25 mg/ml L-MET exhibited no discoloration (<B9 expressed in Pharmacopoeia Eur. standards) after storage for two weeks at 60° C. in the dark. In contrast, solutions of the described compound without the addition of L-MET displayed significant discoloration (B6) under identical conditions.

2. Six months at 40° C. in the dark--Solutions of the described antidepressant compound also containing 0.50 mg/ml L-MET were physically and chemically stable after storage for 6 months at up to 40° C. in the dark. In contrast, solutions of the described compound without the addition of L-MET after 6 months at 30° C. and 40° C. displayed severe discoloration (BY5-6 and BY1-3 respectively), and some diminishment of concentration when stored at 40° C. in the dark.

3. 12 months at 40° C. in the dark--Solutions containing mirtazapine (3 mg/ml) were stabilized for 1 year at 40° C. in the dark, with 0.5 mg/ml of L-MET, while, as described in EXAMPLE I A.2., samples without the stabilizer displayed severe discoloration and diminishment of concentration after 6 months.

4. Destabilization with hydrogen peroxide at 60° C. in the dark--1.5 ml of 0.001% hydrogen peroxide was added to two solutions of 3.0 mg/ml mirtazapine, one containing L-Met (0.5 mg/ml) and the other not. After one week, the solution not containing L-MET was significantly discolored (BY1), while the one containing L-MET was less so (B6). After 2 weeks, the results remained unchanged.

L-MET, at the concentrations tested, was unable to stabilize a solution of mirtazapine in daylight. Therefore, mirtazapine in solution should be protected from light, even if L-MET has been added.

EXAMPLE II

Stabilization of 1,2,3,4,10,14b-hexahydro-2-methyldibenzo[c,f] pyrazino [1,2-a]azepinemonohydrochloride.

1,2,3,4,10,14b-hexahydro-2-methyl-dibenzo [c,f]pyrazino [1,2-a] azepinemonohydrochloride (mianserin) is a compound described in U.S. Pat. No. 3,534,041 to van der Burg, the contents of which are incorporated by this reference. Mianserin and similar compounds may be made according to the teachings of these patents.

Solutions of 3.0 mg/ml mianserin were prepared. The pHs of the solutions were adjusted to 4, and the solutions were sterilized by filtration through a 0.22 micron filter. Aseptic techniques were used throughout the experiments. To one of the solutions, sufficient L-MET was added to bring the concentration of L-MET to 0.5 mg/ml of solution. The samples were stored at 60° C. in the dark, and at room temperature in daylight.

The sample without L-MET stored at 60° C. discolored (BY3) within 1 week's time. Both samples stored in daylight discolored, although the sample without added L-MET was more discolored (B4) than the sample with L-MET (B7). The other sample remained stable during the first week. After 2 weeks time, all samples discolored, although the samples without L-MET discolored more (>BY1 @ 60° C. and B2 with daylight) than the samples containing L-MET (B8 @ 60° C. and B5 with daylight).

EXAMPLE III

Stabilization of amitriptyline HCl with L-methionine

Amitriptyline HCl is readily commercially available from various companies including Merck, Sharpe & Dohme. Solutions containing 3.14 mg/ml of amitriptyline HCl were prepared. As with the other EXAMPLEs tested for two weeks, the pH of the solutions were adjusted to 4 with a citrate buffer, and the solutions were sterilized by filtration through a 0.22 micron filter. Aseptic techniques were used throughout the experiments. To one of the solutions, sufficient L-MET was added to bring the concentration of L-MET to 0.5 mg/ml of solution. The samples were stored at 60° C. in the dark, and at room temperature in daylight. The sample containing L-MET displayed better clarity than the sample not containing L-MET when exposed to daylight ("clear" vs. many particles present respectively) over one week's time. After two weeks time, the sample containing L-MET also had many particles present. All solutions of amitriptyline HCl stored at 60° C. in the dark displayed clarity and no discoloration.

EXAMPLE IV

Stabilization of
2(N)-methyl-1,2,3,4-tetrahydro-9H-dibenzo[a,e]-
pyridino[3,4-c]cycloheptatriene maleate (setiptiline)
with L-methionine Solutions containing 3.77 mg/ml of setipiline (Chemical Abstracts Service registry number 57262-94-9) maleate were prepared. The pHs of the solutions were adjusted to 4, and the solutions were sterilized by filtration through a 0.22 micron filter. Aseptic techniques were used throughout the experiments. To one of the solutions, sufficient L-MET was added to bring the concentration of L-MET to 0.5 mg/ml of solution. The samples were stored at 60° C. in the dark, and at room temperature in daylight. All samples remained stable after one week's time. After two weeks time, the sample without L-MET which was exposed to daylight was no longer clear and contained many particles, while the sample containing L-MET remained clear. All solutions containing setipiline maleate stored at 60° C. in the dark remained clear and exhibited no discoloration.

EXAMPLES V-VIII

Attempts were made to use L-cysteine—0.587 mg/ml (EXAMPLE V), 1,4-dithioerythitol—0.527 mg/ml (EXAMPLE VI), L-tryptophan—0.685 mg/ml (EXAMPLE VII), and cystine—0.807 mg/ml (EXAMPLE VIII) as stabilizers for mirtazapine by substituting these particular compounds, one at a time, for L-MET, and testing the solutions for clarity and discoloration after storage in daylight and at 60° C. in the dark. The solutions with these compounds showed more discoloration than those which contained none of the compound.

EXAMPLES IX-XVI

In a similar manner as described in EXAMPLES I-IV, preparations of mirtazapine mianserin, amitriptyline, or setiptiline may be stabilized with 0.5 mg/ml solutions of D-methionine or DL-methionine.

Reference herein to specific embodiments or examples should not be interpreted as limitations to the scope of the invention, which is defined by the appended claims.

What is claimed is:

1. A stable aqueous preparation comprising: a stabilizer selected from the group consisting of L-methionine, D-methionine, DL-methionine and mixtures thereof in admixture with water and a therapeutically useful concentration of at least one tricyclic nitrogen heterocycle antidepressant capable of stabilization by the selected stabilizer, wherein the stabilizer is present in a concentration sufficient to stabilize the tricyclic nitrogen heterocycle.

2. The stable aqueous preparation of claim 1 wherein the tricyclic nitrogen heterocycle is present in quantities of about 1 to about 5 milligrams per milliliter of admixture.

3. The stable aqueous preparation of claim 1 wherein said stabilizer is an isomer or racemic mixture of methionine, and said tricyclic nitrogen heterocycle is amitriptyline.

4. A method of stabilizing an aqueous preparation of amitriptyline comprising: dissolving into said aqueous preparation a sufficient amount of L-methionine, D-methionine, DL-methionine, or mixtures thereof to stabilize the heterocycle in aqueous solution.

5. A stabilized aqueous solution comprising, in admixture, amitriptyline in an amount of about 1 to about 5 milligrams per milliliter of aqueous solution, and a sufficient amount of L-methionine, D-methionine, DL-methionine or mixtures thereof to stabilize said heterocycle in aqueous solution.

6. The stabilized aqueous solution of claim 5 comprising L-methionine, D-methionine, DL-methionine, or mixtures thereof present in an amount of about 0.05 to about 5 milligrams per milliliter aqueous solution.

7. The stabilized aqueous solution of claim 6 wherein the chemical means for stabilizing the mirtazapine is DL-methionine or L-methionine.

* * * * *